United States Patent
Kou et al.

(10) Patent No.: US 10,669,233 B2
(45) Date of Patent: *Jun. 2, 2020

(54) PROCESS OF PURIFYING METHIONINE

(71) Applicants: SUNRESIN NEW MATERIALS CO. LTD., XI AN, Xian, Shaanxi Province (CN); BLUESTAR ADISSEO NANJING CO., LTD., Nanjing, Jiangsu Province (CN)

(72) Inventors: Xiaokang Kou, Xi'an (CN); Risheng Wang, Xi'an (CN); Gang Wang, Xi'an (CN); Qiong Liu, Xi'an (CN); Wanping Ren, Xi'an (CN); Julien Boutet, Nanjing (CN); Yuanbin Yang, Nanjing (CN); Valentin Guidal, Nanjing (CN)

(73) Assignees: SUNRESIN NEW MATERIALS CO. LTD., XI'AN, Xi'an, Shaanxi (CN); Bluestar Adisseo Nanjing Co., Ltd., Nanjing, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/358,659

(22) Filed: Mar. 19, 2019

(65) Prior Publication Data
US 2019/0210964 A1   Jul. 11, 2019

Related U.S. Application Data

(63) Continuation of application No. 15/740,792, filed on Dec. 28, 2017, now Pat. No. 10,287,244.

(51) Int. Cl.
| | |
|---|---|
| C07C 319/28 | (2006.01) |
| C07C 323/58 | (2006.01) |
| A61K 31/145 | (2006.01) |
| B01J 20/285 | (2006.01) |
| B01D 15/26 | (2006.01) |
| B01D 15/12 | (2006.01) |
| B01D 15/42 | (2006.01) |

(52) U.S. Cl.
CPC .......... C07C 319/28 (2013.01); A61K 31/145 (2013.01); B01D 15/12 (2013.01); B01D 15/265 (2013.01); B01D 15/426 (2013.01); B01J 20/285 (2013.01); C07C 323/58 (2013.01)

(58) Field of Classification Search
CPC .... C07C 319/28; C07C 323/58; B01J 20/285; B01D 15/265; A61K 31/145
See application file for complete search history.

(56) References Cited

U.S. PATENT DOCUMENTS

| | | |
|---|---|---|
| 2008/0045746 A1 | 2/2008 | Takamatsu et al. |
| 2014/0213819 A1 | 7/2014 | Buss et al. |

FOREIGN PATENT DOCUMENTS

| | | |
|---|---|---|
| CN | 103 641 758 A | 3/2014 |
| CN | 103 772 246 A | 5/2014 |
| CN | 104 177 280 A | 12/2014 |
| CN | 104 693 082 A | 6/2015 |
| CN | 104 926 701 A | 9/2015 |
| CN | 104 910 055 A | 9/2019 |
| FR | 2 772 026 A1 | 6/1999 |
| WO | 95/14002 A1 | 5/1995 |

OTHER PUBLICATIONS

Doulia et al.,Journal of Chemical Technology and Biotechnology, Removal of amino acids from water by adsorption on polystyrene resins, 2001, 76, pp. 83-89. (Year: 2001).*
Phenomenex, Technical Tip:Column Loadability, 2017, pp. 1-12 downloaded from https://phenomenex.blog/2017/05/23/technical-tip-column-loadability/ on May 22, 2019. (Year: 2017).*
Moore et al (Journal of Biological Chemistry, Chromatography of Amino Acids on Sulfonated Polystyrene Resins, 1951, pp. 663-681. (Year: 1951).*
Hill (Richard Hill Engineering, Engineering Design Considerations, pp. 1-54, recovered from https://www.soci.org/-/media/Files/Conference.../Richard_Hill_engineering.ashx on Jul. 9, 2018) (Year: 2012).*
Database WPI Week 198304 Thomson Scientific, London, GB AN 1983-09333K & SU 914 548 B (Heteroorg CPDS as USSR9 Mar. 25, 1982 abstract, claims 1-14.
Database WPI Week 201609 Thomson Scientific, London, GB AN 2015-70993X abstract claims 1, 15.
Li, Ang et al.: "Comparison of Refining D-Methionine by Anion-Cation Exchange Resin", Amino Acids & Biotic Resources, vol. 28, No. 2. Jun. 30, 2006, pp. 57-59, XP009507978.

* cited by examiner

Primary Examiner — Paul A Zucker
(74) Attorney, Agent, or Firm — PROI Intellectual Property US

(57) ABSTRACT

The present invention provides a process for purifying methionine. A methionine product having a purity of up to 99% or higher is obtained by separating methionine from a salt by-product through a process comprising adsorption and desorption using a macroporous adsorption resin, where the methionine content in the salt by-product is ≤0.03%. The yield of methionine extracted with the resin is up to 98% or higher. By using the process of the present invention, the existing production process is simplified, the quality of the methionine product is improved, and the production costs for methionine are reduced.

16 Claims, 1 Drawing Sheet

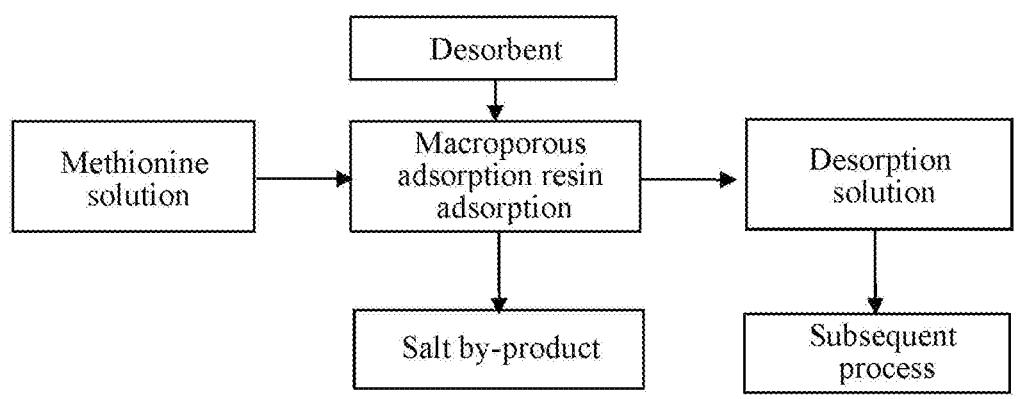

PROCESS OF PURIFYING METHIONINE

BACKGROUND

Technical Field

The present invention relates to the field of chemical industry, and more particularly, to a process for purifying methionine.

Related Art

Methionine is closely related to the metabolism of various sulfur-containing compounds in an organism. Methionine deficiency can cause a loss of appetite, retarded growth or no gain in body weight, renal enlargement and accumulation of iron in the liver, and the like, finally leading to hepatic necrosis or fibrosis. Another type of methionine is a hydroxyl derivative of methionine (that is, liquid methionine), which serves as a methionine nutritional supplement for promoting the growth and development of animals when widely used as a feed additive.

Both methionine and liquid methionine are an amino acid, and differ only in the a position, at which the methionine is linked to —NH2 and the liquid methionine is linked to —OH. When the pH of a solution is <pI (isoelectric point), methionine exists as a cation; when the pH of a solution is >pI, methionine exists as an anion; and when the pH is equal to pI, the solubility is the minimum. Methionine is soluble in water, but poorly soluble in non-polar solvents, and has a rather high melting point. An aqueous solution of methionine is similar in nature to an aqueous solution with a high dipole moment. According to the C—S—C structure in the molecular structure of methionine, methionine can be well separated from a salt by-product by selectively adsorbing methionine onto a non-polar macroporous adsorption resin by making full use of the differential binding to the resin of methionine and salt compounds.

At present, the method for producing methionine in industry is mainly Hydantion, and the method for producing liquid methionine is mainly acrolein method. Both methods have the process requirement of separating the methionine solution from a salt by-product during the production process. There is no effective desalination means in the existing production methods, resulting in the eduction of a large amount of salt substances accompanying the crystallization of the product, thereby affecting the quality and yield of the product, and increasing the production costs of methionine.

Chinese Patent No. 201310317849.2 entitled "METHOD AND APPARATUS FOR REMOVING IMPURITIES IN SECONDARY METHIONINE MOTHER LIQUOR" discloses a method and an apparatus for removing impurities in a secondary methionine mother liquor by using diatomaceous earth, activated carbon or activated clay. These adsorbents have low adsorption efficiency, and cannot be recycled effectively after adsorption, resulting in secondary pollution to the environment and thus being unsuitable for industrial applications. Chinese Patent No. 201310194709.5 entitled "PROCESS FOR PRODUCING METHIONINE" discloses a process for separating a methionine crystallization mother solution, in which the methionine crystallization mother solution is separated by a continuous chromatographic separation system filled with a sodium or potassium chromatography resin, to obtain a methionine solution and an inorganic salt solution. This method is only applicable to a crystallization mother liquor with a lower methionine content and not validated for the separation of a high content of a methionine solution from a salt by-product in industrialized production, and no effective solution is provided.

SUMMARY

An objective of the present invention is to provide a process for purifying methionine.

Methionine is separated from a salt by-product by using a macroporous adsorption resin, in which the methionine is adsorbed onto the macroporous adsorption resin, and then the methionine is recovered by desorbing from the resin using a desorbent; and the salt by-product is not absorbed onto the macroporous adsorption resin during the adsorption process, but enters an effluent resulting from the adsorption. The process mainly comprises the following steps:

1) resin adsorption: adjusting the pH of a methionine solution, flowing the methionine solution, from the top to the bottom, through a macroporous adsorption resin layer at a certain flow rate, and stopping resin adsorption when the content of methionine in an effluent from the resin column is greater than or equal to 10% (w/w) of the content at an inlet, in which the effluent resulting from the resin adsorption is a salt by-product;

2) resin desorption: desorbing, from the top to the bottom, the resin that has completed the adsorption in step 1) using a certain volume and concentration of a desorbent at a certain flow rate, and collecting the desorption solution; and 3) subsequent process: subjecting the desorption solution to subsequent treatments following an existing process.

In the process for purifying methionine, the methionine comprises methionine and a hydroxyl derivative of methionine (that is, liquid methionine).

In the process for purifying methionine, the salt by-product is one of sodium carbonate, sodium sulfate, ammonium sulfate, potassium carbonate, or potassium sulfate, or a mixture of two or more thereof.

In the process for purifying methionine, the methionine solution to be adsorbed is adjusted to pH 1.0-10.0, preferably, pH 1.0-5.0, and more preferably, pH 2.0-3.0.

In the process for purifying methionine, the methionine solution is flowed through the macroporous adsorption resin layer at a flow rate of 1-10 BV/h, preferably, 1-5 BV/h, and more preferably, 1-3 BV/h.

In the process for purifying methionine, the desorbent is one of sodium hydroxide, hydrochloric acid, sodium chloride, aqueous ammonia, methanol, ethanol, i-propanol, or acetone.

The concentration of the desorbent is 1-10% (w/w), preferably, 2-8% (w/w), and more preferably, 4-8% (w/w).

The volume of the desorbent for the resin is 1-3 BV.

The flow rate of the desorbent for the resin is 1-5 BV/h.

In a more preferred implementation of the present invention, the methionine comprises methionine and a hydroxyl derivative of methionine, and the salt by-product is one of sodium carbonate, sodium sulfate, ammonium sulfate, potassium carbonate, or potassium sulfate, or a mixture of two or more thereof.

In the resin adsorption of step 1), the methionine solution to be adsorbed is adjusted to pH 2.0-3.0; and then the methionine solution is flowed through the macroporous adsorption resin layer at a flow rate of 1-3 BV/h.

The desorbent is selected from sodium hydroxide, potassium hydroxide, hydrochloric acid, sodium chloride, aqueous ammonia, methanol, ethanol, i-propanol, and acetone.

The concentration of the desorbent is 4-8% w/w;

The volume of the desorbent for the resin is 1-3 BV.

The flow rate of the desorbent for the resin is 1-5 BV/h.

In the present invention, BV refers to a volume of a resin bed loaded in a resin column, that is, a bed volume, referred to as BV in short. 1 BV refers to 1-fold bed volume, and 2 BV refers to 2-fold bed volumes.

The present invention relates to a process for purifying methionine. Specifically, a methionine product having a purity of up to 99% is obtained by separating methionine from a salt by-product through a process comprising adsorption and desorption using a macroporous adsorption resin, where the methionine content in the salt by-product is 0.03%. The yield of methionine extracted with the resin is ≥98% (w/w). By using the process of the present invention, the existing production process is simplified, the quality of the methionine product is improved, and the production costs for methionine are reduced.

Since currently there is no available process for purifying methionine and liquid methionine, the present process is inventive and of great economic benefit.

BRIEF DESCRIPTION OF THE DRAWINGS

The drawing shows a specific implementation of a process according to the present invention.

DETAILED DESCRIPTION

The present invention is further described by way of examples, in which the methionine solution used is available from two enterprises in Chongqing and Nanjing, respectively.

Example 1

1. Resin adsorption: A methionine solution (pH 10.72) with a methionine content of 17.24% (w/w) and a sodium carbonate content of 10.35% (w/w) was flowed evenly, from the top to the bottom, through a 100 ml resin bed of a macroporous adsorption resin trademarked as XDA-1 by Xi'An Sunresin New Materials Co., Ltd at a flow rate of 1 BV/h. An effluent from the resin column was collected separately, and feeding to the resin column was stopped when the methionine content in the effluent from the bottom of the resin column is 1.7% (w/w).

2. Resin desorption: The resin was desorbed from the top to the bottom using 2 BV of a 3% (w/w) sodium hydroxide solution at a flow rate of 1 BV/h, and the desorption solution was collected.

3. 300 ml of the effluent from the resin column was collected, and detected to have a methionine content of 0.02% (w/w), and a sodium carbonate content of 10.35% (w/w). 200 ml of the desorption solution was collected, and detected to have a methionine content of 24.60% (w/w), with a methionine yield of 95.15% (w/w).

Example 2

1. Resin adsorption: A liquid methionine solution with a methionine content of 2.8% (w/w) and a potassium sulfate content of 17.4% (w/w) was adjusted to pH 2.2 with a 2% (w/w) sulfuric acid solution, and flowed evenly, from the top to the bottom, through a 100 ml resin bed of a macroporous adsorption resin trademarked as XDA-8 by Xi'An Sunresin New Materials Co., Ltd at a flow rate of 1 BV/h. An effluent from the resin column was collected separately, and feeding to the resin column was stopped when the methionine content in the effluent from the bottom of the resin column is 0.3% (w/w).

2. Resin desorption: The resin was desorbed from the top to the bottom using 3 BV of a 4% (w/w) methanol solution at a flow rate of 1 BV/h, and the desorption solution was collected.

3. 700 ml of the effluent from the resin column was collected, and detected to have a methionine content of 0.01% (w/w), and a potassium sulfate content of 17.38% (w/w). 302 ml of the desorption solution was collected, and detected to have a methionine content of 6.45% (w/w), with a methionine yield of 98.76% (w/w).

Examples 3-9

The implementation process was specifically the same as that in Example 1, in which the influence of different pH values of the methionine solutions on the adsorption capacity of the resin was mainly investigated, where the concentrations not specifically given in the experiments were all concentrations in percentages by weight.

Methionine content: 2.80% (w/w), ammonium sulfate content: 43.5% (w/w), and potassium carbonate content: 2.1% (w/w). Feed volume: 7 BV, and feed flow rate: 1 BV/h. 5 portions of macroporous adsorption resin trademarked as XDA-8 by Xi'An Sunresin New Materials Co., Ltd were prepared, each portion containing 100 ml resin. The methionine solution was adjusted to pH 1.0, 3.0, 7.0, 9.0, and 10.0 respectively with a 4% (w/w) sodium hydroxide or a 4% (w/w) sulfuric acid solution, and then subjected to an adsorption comparison test.

Adsorption capacity of resin=(Methionine content in the feed*Feed volume−Methionine content in the effluent*Effluent volume)/Resin volume

| Example | pH of mother solution | Adsorption capacity of resin (g/L) |
| --- | --- | --- |
| Example 3 | 1.0 | 192.1 |
| Example 4 | 2.0 | 195.9 |
| Example 5 | 3.0 | 194.1 |
| Example 6 | 5.0 | 172.5 |
| Example 7 | 7.0 | 159.4 |
| Example 8 | 9.0 | 102.1 |
| Example 9 | 10.0 | 80.2 |

Examples 10-15

The implementation process was specifically the same as that in Example 1, in which the influence of different adsorption rates on the adsorption capacity of the resin was mainly investigated, where the concentrations not specifically given in the experiments were all concentrations in percentages by weight.

Methionine content: 3.28% (w/w), sodium sulfate content: 40.19% (w/w), pH 2.40. Feed volume: 7 BV. 5 portions of macroporous adsorption resin trademarked as XDA-8 by Xi'An Sunresin New Materials Co., Ltd were prepared, each portion containing 100 ml resin. The resin adsorption was carried out at various flow rates.

| Example | Flow rate (BV/h) | Adsorption capacity of resin (g/L) |
| --- | --- | --- |
| Example 10 | 1 | 229.6 |
| Example 11 | 2 | 225.1 |
| Example 12 | 3 | 211.9 |
| Example 13 | 5 | 139.2 |

| Example | Flow rate (BV/h) | Adsorption capacity of resin (g/L) |
|---|---|---|
| Example 14 | 7 | 91.4 |
| Example 15 | 10 | 55.8 |

Examples 16-24

The implementation process was specifically the same as that in Example 1, in which the desorption rate of various desorbents and the quality of the desorption solution were mainly investigated, where the concentrations not specifically given in the experiments were all concentrations in percentages by weight.

Methionine content: 2.95% (w/w), ammonium sulfate content: 42.04% (w/w), pH 2.20. Feed volume: 7 BV each. The methionine solution was flowed respectively through 7 portions of macroporous adsorption resin (each 100 ml) trademarked as XDA-300 by Xi'An Sunresin New Materials Co., Ltd at a flow rate of 1 BV/h. After adsorption, the resin was desorbed by using 3 BV of 4% (w/w) sodium hydroxide, 4% (w/w) potassium hydroxide, 4% (w/w) hydrochloric acid, 4% (w/w) sodium chloride, 4% (w/w) aqueous ammonia, 4% (v/v) methanol, 4% (v/v) ethanol, 4% (v/v) i-propanol, and 4% (v/v) acetone at a flow rate of 1 BV/h respectively.

| Example | Desorption solution | Methionine concentration in the desorption solution (%) | Ammonium sulfate concentration in the desorption solution (%) | Desorption rate (%) |
|---|---|---|---|---|
| Example 16 | 4% (w/w) sodium hydroxide | 6.03 | 0.03 | 87.6 |
| Example 17 | 4% (w/w) potassium hydroxide | 5.98 | 0.02 | 86.9 |
| Example 18 | 4% (w/w) hydrochloric acid | 5.81 | 0.01 | 84.4 |
| Example 19 | 4% (w/w) sodium chloride | 5.21 | 0 | 75.7 |
| Example 20 | 4% (w/w) aqueous ammonia | 6.69 | 0.02 | 97.3 |
| Example 21 | 4% (v/v) methanol | 6.79 | 0.02 | 98.7 |
| Example 22 | 4% (v/v) ethanol | 6.75 | 0.05 | 98.1 |
| Example 23 | 4% (v/v) i-propanol | 6.84 | 0.02 | 99.4 |
| Example 24 | 4% (v/v) acetone | 6.84 | 0.01 | 99.4 |

Examples 25-29

The implementation process was specifically the same as that in Examples 16-24, in which the influences of different concentrations of a desorbent on the quality of the desorption solution and the desorption rate were mainly investigated.

Methionine content: 2.64% (w/w), ammonium sulfate content: 42.04% (w/w), pH 2.20. Feed volume: 8 BV each. The methionine solution was flowed respectively through 4 portions of macroporous adsorption resin (each 100 ml) trademarked as XDA-8G by by Xi'An Sunresin New Materials Co., Ltd at a flow rate of 1 BV/h. After adsorption, the resin was desorbed by using 3 BV of 1% (w/w) aqueous ammonia, 2% (w/w) aqueous ammonia, 4% (w/w) aqueous ammonia, 8% (w/w) aqueous ammonia, and 10% (w/w) aqueous ammonia at a flow rate of 1 BV/h respectively.

| Example | Desorption solution | Methionine concentration in the desorption solution (%) | Desorption rate (%) |
|---|---|---|---|
| Example 25 | 1% (w/w) aqueous ammonia | 6.03 | 85.59 |
| Example 26 | 2% (w/w) aqueous ammonia | 6.69 | 95.02 |
| Example 27 | 4% (w/w) aqueous ammonia | 6.97 | 99.00 |
| Example 28 | 8% (w/w) aqueous ammonia | 6.95 | 98.73 |
| Example 29 | 10% (w/w) aqueous ammonia | 6.55 | 93.04 |

Examples 30-33

The implementation process was specifically the same as that in Examples 16-24, in which the influences of different volumes of a desorbent on the desorption rate were mainly investigated.

Methionine content: 3.07%, ammonium sulfate content: 44.55%, pH 2.41. Feed volume: 7 BV each. The methionine solution was flowed respectively through 4 portions of macroporous adsorption resin (each 100 ml) trademarked as XDA-200 by Xi'An Sunresin New Materials Co., Ltd at a flow rate of 1 BV/h.

| Example | Volume of desorption solution | Methionine concentration in the desorption solution (%) | Desorption rate (%) |
|---|---|---|---|
| Example 30 | 1 BV | 12.47 | 58.03 |
| Example 31 | 2 BV | 8.75 | 81.47 |
| Example 32 | 3 BV | 6.99 | 97.79 |
| Example 33 | 5 BV | 4.21 | 98.02 |

Examples 34-37

The implementation process was specifically the same as that in Examples 16-24, in which the influences of different volumes of a desorbent on the desorption rate were mainly investigated.

Methionine content: 2.58% (w/w), ammonium sulfate content: 44.55% (w/w), pH 2.41. Feed volume: 8 BV each.

The methionine solution was flowed respectively through 4 portions of macroporous adsorption resin (each 100 ml) trademarked as XDA-300 by Xi'An Sunresin New Materials Co., Ltd at a flow rate of 1 BV/h. After adsorption, the resin was desorbed by using 3 BV of 4% (w/w) acetone solution at a flow rate of 1 BV/h, 3 BV/h, 7 BV/h, and 10 BV/h respectively.

| Example | Flow rate of the desorption solution (BV/h) | Methionine concentration in the desorption solution (%) | Desorption rate (%) |
|---|---|---|---|
| Example 34 | 1 | 6.79 | 98.72 |
| Example 35 | 3 | 6.78 | 98.55 |
| Example 36 | 7 | 5.55 | 80.71 |
| Example 37 | 10 | 4.84 | 70.36 |

Example 38

1. Resin adsorption: A methionine solution (pH 2.75) with a methionine content of 2.98% (w/w) and an ammonium sulfate content of 41.59% (w/w) was flowed evenly, from the top to the bottom, through a 100 ml resin bed of a macroporous adsorption resin trademarked as XDA-1 by Xi'An Sunresin New Materials Co., Ltd at a flow rate of 1 BV/h. An effluent from the resin column was collected separately, and feeding to the resin column was stopped when the methionine content in the effluent from the bottom of the resin column is 0.3% (w/w).
2. Resin desorption: The resin was desorbed from the top to the bottom using 3 BV of a 6% (w/w) aqueous ammonia solution at a flow rate of 1 BV/h, and the desorption solution was collected.
3. 750 ml of the effluent from the resin column was collected, and detected to have a methionine content of 0.01% (w/w), and an ammonium sulfate content of 41.55% (w/w). 300 ml of the desorption solution was collected, and detected to have a methionine content of 6.75% (w/w), with a methionine yield of 98.18% (w/w).

What is claimed is:

1. A process for purifying methionine, wherein methionine is separated from a salt by-product by using a macroporous adsorption resin, in which the methionine is adsorbed onto the macroporous adsorption resin, and then the methionine is recovered by desorbing from the resin using a desorbent; and the salt by-product is not absorbed onto the macroporous adsorption resin during the adsorption process, but enters an effluent resulting from the adsorption, the process comprising the following steps:
   1) flowing a methionine solution comprising methionine and a salt by-product being at least one of sodium carbonate, sodium sulfate, ammonium sulfate, potassium carbonate, ammonium carbonate, or potassium sulfate, or a mixture of two or more thereof, from the top to the bottom, through a macroporous adsorption resin layer, and stopping resin adsorption when the content of methionine in the effluent from the resin column is 1 to 50% (w/w) of the content at the inlet, in which the effluent resulting from the resin adsorption is a salt by-product;
   2) resin desorption: desorbing, from the top to the bottom, the resin that has completed the adsorption in step 1) using a desorbent, and collecting the desorption solution; and
   3) subsequent process: subjecting the desorption solution to subsequent treatments following an existing process.

2. The process for purifying methionine according to claim 1, wherein the methionine is selected from methionine and a hydroxyl derivative of methionine.

3. The process for purifying methionine according to claim 1, wherein in the resin adsorption of step 1), the methionine solution to be adsorbed is adjusted to pH 1.0-10.0.

4. The process for purifying methionine according to claim 3, wherein in the resin adsorption of step 1), the methionine solution to be adsorbed is adjusted to pH 1.0-5.0.

5. The process for purifying methionine according to claim 4, wherein in the resin adsorption of step 1), the methionine solution to be adsorbed is adjusted to pH 2.0-3.0.

6. The process for purifying methionine according to claim 1, wherein the methionine solution is flowed through the macroporous adsorption resin layer at a flow rate of 1-10 BV/h.

7. The process for purifying methionine according to claim 6, wherein the methionine solution is flowed through the macroporous adsorption resin layer at a flow rate of 1-5 BV/h.

8. The process for purifying methionine according to claim 7, wherein the methionine solution is flowed through the macroporous adsorption resin layer at a flow rate of 1-3 BV/h.

9. The process for purifying methionine according to claim 1, wherein the desorbent is selected from sodium hydroxide, potassium hydroxide, acetic acid, acetonitrile, sulfuric acid, nitric acid, bromohydric acid, hydrochloric acid, sodium chloride, aqueous ammonia, methanol, ethanol, i-propanol, isobutanol, ethyl acetate, and acetone.

10. The process for purifying methionine according to claim 1, wherein the concentration of the desorbent is 1-50% (w/w) with respect to the desorbent solution.

11. The process for purifying methionine according to claim 10, wherein the concentration of the desorbent is 1-30% (w/w) with respect to the desorbent solution.

12. The process for purifying methionine according to claim 11, wherein the concentration of the desorbent is 2-25% (w/w) with respect to the desorbent solution.

13. The process for purifying methionine according to claim 1, wherein the volume of the desorbent for the resin is 1-10 BV.

14. The process for purifying methionine according to claim 1, wherein the flow rate of the desorbent for the resin is 1-10 BV/h.

15. The process for purifying methionine according to claim 1, wherein
   in the resin adsorption of step 1), the methionine solution to be adsorbed is adjusted to pH 1.0-3.0; and then the methionine solution is flowed through the macroporous adsorption resin layer at a flow rate of 1-10 BV/h;
   the desorbent is selected from sodium hydroxide, potassium hydroxide, hydrochloric acid, sodium chloride, aqueous ammonia, methanol, ethanol, i-propanol, and acetone;
   the concentration of the desorbent is 2-25% (w/w);
   the volume of the desorbent for the resin is 1-3 BV; and
   the flow rate of the desorbent for the resin is 1-5 BV/h.

16. The process for purifying methionine according to claim 1, comprising the following steps:
   1) resin adsorption: flowing a methionine solution (pH 1.5) with a methionine content of 2.98% (w/w) and an ammonium sulfate content of 41.59% (w/w) evenly, from the top to the bottom, through a 100 ml resin bed of a macroporous adsorption resin trademarked as XDA-1 by Xi'An Sunresin New Materials Co., Ltd at a flow rate of 1 BV/h, collecting the effluent from the resin column separately, and stopping feeding to the resin column when the methionine content in the effluent from the bottom of the resin column is 0.3%;

2) resin desorption: desorbing, from the top to the bottom, the resin using 3 BV of 12% aqueous ammonia solution at a flow rate of 1 BV/h, and collecting the desorption solution;

this desorbing solution is collected and sent back to the methionine process with improvement of recycling yield, economical balance, environmental footprint and a simplification of the process; and 3) the resin is regenerated by washing step and prepared for new adsorption with adsorbed solution.

* * * * *